United States Patent [19]
Allec et al.

[11] Patent Number: 5,660,839
[45] Date of Patent: Aug. 26, 1997

[54] NONGREASY/NONSTICKY FATTY COSMETIC/DERMATOLOGICAL COMPOSITIONS

[75] Inventors: Josiane Allec, Antibes; Eve Ferrara, Le Cannet; Isabelle Bara, Paris, all of France

[73] Assignee: L'Oreal, Paris, France

[21] Appl. No.: 500,594

[22] Filed: Jul. 11, 1995

[30] Foreign Application Priority Data

Jul. 11, 1994 [FR] France .................... 94 08569

[51] Int. Cl.$^6$ .............. A61K 7/48; A61K 7/06; A61K 7/02
[52] U.S. Cl. ............ 424/401; 424/70.1; 424/78.03; 424/65; 424/63; 424/59; 424/47; 424/497; 514/844; 514/845; 514/937; 514/944; 514/969
[58] Field of Search .................. 424/401, 70.1, 424/78.03, 63, 59, 47, 65, 497; 514/844, 845, 944, 969, 937

[56] References Cited
FOREIGN PATENT DOCUMENTS

| 0566442 | 10/1993 | European Pat. Off. . |
| 0605284 | 7/1994 | European Pat. Off. . |
| 2521003 | 8/1976 | Germany . |

OTHER PUBLICATIONS

Patent Abstracts of Japan, vol. 10, No. 31 (C–327) (2088) & JP–A–60 184 004 (Pola Kaset K.K.K.) (1985).

*Primary Examiner*—Jyothsna Venkat
*Attorney, Agent, or Firm*—Burns, Doane, Swecker & Mathis, L.L.P.

[57] ABSTRACT

Nongreasy, nonsticky cosmetic and/or dermatological compositions for topical application to human skin and/or hair, characteristically without imparting a shiny appearance thereto, contain at least one fatty substance and an amount of deformable hollow particulates effective to avoid the greasy and/or sticky feel otherwise attributable to the at least one fatty substance, said deformable hollow particulates comprising a copolymer of vinylidene chloride, acrylonitrile and a (meth)acrylic comonomer and having a particle size ranging from 1 µm to 250 µm.

15 Claims, No Drawings

NONGREASY/NONSTICKY FATTY COSMETIC/DERMATOLOGICAL COMPOSITIONS

BACKGROUND OF THE INVENTION

1. Technical Field of the Invention

The present invention relates to novel cosmetic and/or dermatological compositions comprising deformable hollow particulates and fatty substances or agents, i.e., lipophilic materials such as oils and/or waxy compounds, water-in-oil or oil-in-water emulsions, lipophilic gels, pastes or anhydrous cast products.

This invention also relates to novel cosmetic/dermatological compositions useful for the makeup, care and hygiene of human skin, both of the face and of the human body, including the scalp and the mucosae, haircare and also for the therapeutic treatment of the skin and the mucosae. Thus, the compositions of the invention can comprise, inter alia, a skin or haircare cream, a balm, a lotion, a gel, an ointment, a blush or a fluid or cast makeup foundation, a dermopharmaceutical ointment, a cleansing or makeup removal milk, or a deodorant or sunscreen.

2. Description of the Prior Art

Cosmetic/dermatological compositions having a high content of oil, and more especially those having a continuous fatty phase, tend to deposit on the skin a film with a greasy, sticky or tacky feel, often accompanied by a shiny appearance, making them unattractive or even preventing their use. This is particularly the case when repeated applications are required on the scalp or face, and more especially for users or patients having greasy skin or skin afflicted with acne. Furthermore, the presence of a large amount of fats makes it difficult to spread the composition on the skin.

In point of fact, a large number of cosmetic and/or dermatological active agents can be formulated only in the presence of a large amount of fats, and in particular in an anhydrous medium or a medium having a continuous fatty phase. This is, in particular, the case with active agents which are unstable in water. In addition, some compositions intended for dry or even very dry skins require the presence of a continuous fatty phase.

Thus, serious need continues to exist in this art for cosmetic and/or dermatological compositions containing fatty substances, and even lipophilic active agents, which do not impart a sensation of greasiness and/or stickiness to the skin, or a shiny appearance.

SUMMARY OF THE INVENTION

It has now surprisingly and unexpectedly been determined that the greasy and/or sticky feel on the skin of compositions rich in fatty substances can be markedly reduced by formulating therein deformable hollow particles having a particular density and particle size.

In addition to eliminating such greasy feel and/or sticky feel, these particulates impart softness and homogeneity on application (which is very important for a makeup product), as well as a greater ease of spreading.

Briefly, the present invention features incorporating deformable hollow particles into cosmetic and/or dermatological compositions containing fatty substances, for markedly reducing or eliminating the sticky and/or greasy feel attributed to these fatty substances, said particles having a particle size ranging from 1 µm to 250 µm and comprising a copolymer of vinylidene chloride, acrylonitrile and a (meth)acrylate comonomer.

DETAILED DESCRIPTION OF BEST MODE AND PREFERRED EMBODIMENTS OF THE INVENTION

More particularly according to the present invention, by the term "deformable" is intended that the particles are flexible and elastic, namely, after compression or squeezing, they recover their initial shape.

While published French Patent Application No. 93/00,990 describes including hollow particles in a cosmetic or dermopharmaceutical composition to render same less sticky, creamy and soft, the compositions described are aqueous gels devoid of fatty substances. In addition, this '990 application suggests eliminating fatty substances, and hence the source of the greasy and/or sticky feel.

According to the present invention, however, an essentially or virtually anhydrous composition is provided, containing less than 10% of water relative to the total weight thereof. Given this small percentage of water, it is profoundly unexpected to avoid any greasy or sticky feel on the skin. Moreover, the compositions of the invention enable the skin to be treated cosmetically and/or dermatologically, depending on the biologically active agent(s) employed, while hydrating it, nourishing it and/or protecting it.

Advantageously, the subject particulates have a particle size of less than 100 µm. Indeed, the finer the particles, the softer the composition on application. Preferably, the particles have a particle size ranging from 10 µm to 50 µm.

Also advantageously, the particles have a density ranging from 15 $kg/m^3$ to 200 $kg/m^3$, and, preferably, greater than 40 $kg/m^3$ and/or less than 100 $kg/m^3$, and in particular ranging from 60 $kg/m^3$ to 80 $kg/m^3$.

The copolymers of the invention advantageously comprise from 1% to 60% of recurring structural units derived from vinylidene chloride, from 20% to 90% of recurring structural units derived from acrylonitrile and from 1% to 50% of recurring structural units derived from a (meth) acrylic monomer, the sum of the percentages (by weight) being equal to 100. The (meth)acrylic monomer is, for example, a methyl acrylate or methacrylate, and especially the methacrylate. The particles comprised thereof exist, in particular, in the dry or hydrated state.

The aforesaid copolymers are nontoxic and nonirritating to the skin.

Preferably, the particles are in the form of hollow microspheres or microbeads.

The particles of the invention can be prepared, for example, via the processes described in EP-56,219, EP-348,372, EP-486,080, EP-320,473, EP-112,807 and U.S. Pat. No. 3,615,972.

The internal cavity of the particles contains, in principle, a gas which can be air, nitrogen, or a hydrocarbon such as isobutane or isopentane.

The hollow particles according to the present invention are, preferably, those having a particle size of 18 µm and a density of 60 $kg/m^3$ to 80 $kg/m^3$, referred to below as EL 23. These particles impart the maximum of cosmetic qualities. In addition, they present the advantage that they can be incorporated into formulations having a fairly low viscosity (on the order of 20 ps, equivalent to 2 mPa.s) without promoting "creaming" or "blooming" of the particles at the surface of the medium, in contrast to particles of lower density.

Other suitable particulates according to this invention are those marketed under the trademark EXPANCEL by Nobel Casco, such as EXPANCEL 551 DE 20 having a particle size of about 30 μm and a density of about 65 kg/m³, and EXPANCEL 551 DE 50 having a particle size of 40 μm.

The majority of the desirable properties of the particles of the invention can be attributed to their deformability.

In the compositions of the invention, it is preferable to incorporate from 0.1% to 10% by weight of particles, more preferably from 0.5% to 5% by weight, and even more preferably from 0.5% to 2%, relative to the total weight of the composition.

Moreover, these particles have the ability to opacify anhydrous gels and emulsions having an oily continuous phase which are translucent, imparting a white or ivory, shiny, creamy appearance to the composition, thereby enhancing its attractiveness to the consumer. In particular, it has now been determined that the opacifying capacity of the hollow particles according to the invention is greater than that of several other types of particles. Thus, a white cream is obtained with 1% by weight of the hollow particles according to the invention, whereas at least 2% by weight of the other types of particles are required. In particular, even with 4% by weight of MICROPEARL M305 marketed by SEPPIC, which are spherical particles of crosslinked poly (methyl methacrylate) 5 μm to 20 μm in size, a greyish gel is obtained which is unacceptable from the standpoint of visual appearance.

The thermoplastic deformable hollow particles may be introduced into compositions of the water-in-oil, water-in-silicone or oil-in-water emulsion type, anhydrous compositions, lipophilic gels or, alternatively, oily solutions. These compositions are semi-solid or solid.

The oils, waxy compounds, gelling agents and surfactants required for the formulation and stabilization of these compositions are those traditionally employed in the cosmetic and/or dermatological arts.

The oils and/or waxy compounds constitute from 0.5% to 99.9% of the total weight of the composition, preferably from 1% to 80%, and, more preferably, from 1% to 40%. The amount of oil and/or wax depends on the actual form or physical state of the composition.

Exemplary of such oils are mineral oils (petrolatum); vegetable oils (sweet almond, macadamia, blackcurrant-pip oil); synthetic oils such as perhydrosqualene, fatty alcohols, acids or esters (octyl palmitate, isopropyl lanolate, triglycerides including those of capric/caprylic acids), oxyethylenated or oxypropylenated fatty esters and ethers; and silicone oils (cyclomethicone, polydimethylsiloxanes or PDMS) or fluorinated oils.

Exemplary waxy compounds include jojoba oil, paraffin, carnauba wax and beeswax.

Exemplary gelling agents include modified clays (bentones), metal salts of fatty acids (aluminum stearate), ethylene/acrylate copolymers, silicas, polyethylenes, calcium silicates or, alternatively, ethyl cellulose.

And exemplary surfactants (emulsifying and coemulsifying) include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (K or Na alkyl phosphate).

The compositions of the invention can also contain various ingredients traditionally employed in the cosmetic, dermatological and dermopharmaceutical arts, such as coloring agents (pigments, dyes, colorants), solvents, preservatives, perfumes and fragrances, hydrating active agents, ultraviolet ray-absorbing agents (sunscreen or sunblock agents, pigments), pulverulent agents other than the deformable hollow particles, bactericidal agents, antiperspirants and/or odor absorbers. The colorants are advantageously iron oxides, titanium oxides and zinc oxides, typically nanopigments thereof.

These compositions can, in addition, contain one or more hydrophilic, and, preferably, lipophilic, cosmetic or dermatological active agents, in particular for the purpose of treating and/or preventing skin afflictions such as acne, mycoses, eczema, rosacea, seborrhoeic dermatitis, solar dermatoses, skin aging and also scalp complaints. These compositions are formulated to treat the skin topically.

The compositions of the invention advantageously contain one or more cosmetic and/or dermatological biologically active agents. Exemplary of such active agents are:

(a) active agents modulating differentiation and/or proliferation and/or skin pigmentation, such as retinoic acid and isomers thereof; retinol and esters thereof, as well as synthetic compounds such as 6-[3-(1-adamantyl)-4-methoxyphenyl]-2-naphthoic acid; vitamin D and derivatives thereof; estrogens such as estradiol; kojic acid or hydroquinone;

(b) antibacterials such as clindamycin phosphate, erythromycin or antibiotics of the tetracycline class;

(c) antiparasitics, especially metronidazole, crotamiton or pyrethrinoids;

(d) antifungals, especially imidazole compounds such as econazole, ketoconazole or miconazole or salts thereof, polyene compounds such as amphotericin B, compounds of the allylamine family such as terbinafine, or octopirox;

(e) steroidal anti-inflammatory agents such as hydrocortisone, betamethasone valerate or clobetasol propionate, or non-steroidal anti-inflammatory agents such as ibuprofen and salts thereof, diclofenac and salts thereof, polyunsaturated fatty acid compounds such as the amides of 5,8,11-eicosatrienoic acid, acetylsalicylic acid, paracetamol or glycyrrhetinic acid;

(f) anesthetic agents such as lidocaine hydrochloride and derivatives thereof;

(g) antipruritic agents such as thenaldine, trimeprazine or cyproheptadine;

(h) antiviral agents such as acyclovir;

(i) keratolytic agents such as alpha- and beta-hydroxycarboxylic or beta-ketocarboxylic acids, the salts, amides or esters thereof and more especially salicylic acid and derivatives thereof, such as 5-n-octanoylsalicylic acid, α-hydroxy acids such as glycolic acid, lactic acid, citric acid and, in general, fruit acids;

(j) anti-free-radical agents such as alpha-tocopherol or esters thereof, superoxide dismutases, certain metal-chelating agents or ascorbic acid and esters thereof;

(k) antiseborrhoeic agents such as progesterone;

(l) antidandruff agents such as octopirox or pyrithione salts, in particular the zinc or sodium salt;

(m) anti-acne agents such as retinoic acid or benzoyl peroxide;

(n) vitamins (F);

(o) anthranoids such as 1,8,10-tripropionyl-9-anthrone;

(p) cicatrizing agents such as vitamin C;

(q) odor absorbers.

The concentration of biologically active agent in the composition depends on the nature of the active agent; it generally ranges from 0.0001% to 20% by weight relative to the total weight of the composition.

These active agents may be used pure or encapsulated in spherules such as micro- or nanospheres, micro- or nanocapsules, micro- or nanosponges, or lipid vesicles containing ionic and/or nonionic lipids commonly designated liposomes. The encapsulation techniques are traditional to the cosmetic and/or dermatological arts, and are described, in particular, in FR-A-2,315,991 and FR-A-2,485,921.

In order to further illustrate the present invention and the advantages thereof, the following specific examples are given, it being understood that same are intended only as illustrative and in nowise limitative.

In said examples to follow, several fillers of different types were tested in the same anhydrous medium for the purpose of comparing their influence on the texture and opacification of the medium. Some were employed at the minimum concentration for obtaining the opacifying effect. For fillers not providing a satisfactory result, their concentration was gradually increased to 6% by weight. The composition of the anhydrous medium, by weight, was as follows:

(i) Perhydrosqualene 70%

(ii) Silicone fluid 245 marketed by Dow Corning 20%

(iii) Aerosil R972 from Degussa 8% () Trimethylsiloxane-treated hydrophobic pyrogenic silica.

The results obtained are reported in Table 1 below. It will be seen from this Table that only Expancel particles provided the gel with a nongreasy, nonsticky feel and imparted thereto the appearance of a cream, without release of oil, and, hence, a good stability.

TABLE 1

| Type of filler | Percent-age used | Results Appearance | Feel |
|---|---|---|---|
| Micropearl M100 Spherical polymethacrylate powder 8 µm to 10 µm in size Density: 1.2 | 2% gel still translucent and not matted. 6% begins to opacify | Opalescent gel displaying an oily release at the surface | Waxy on application, especially towards the end. Penetrates slowly. |
| Luzenac 15 Mod (talc) | 4% | Greyish and opalescent gel | Greasy. Does not penetrate. Clings on application |
| Orgasol 2002 UD NAT COS Nylon microsponges 2 µm to 10 µm in size | 3% | White cream gel, displaying an oily release. | Slippery, does not penetrate very well. Soft feel. |
| TiO₂ U.S.P. BC Micronized titanium dioxide (Whittaker Clark) | 3% | White cream, shiny but presence of granules. | Greasy, penetrates rapidly and sticky feel which clings on application. |
| EI 23 particles | 1% | Ivory cream, shiny. | Slippery. Slow penetration. Nongreasy feel. |
| Expancel 551 DE 20 | 1% | Off-white, shiny cream. | Moderate penetration. Slippery. Soft final feel, not sticky, |

TABLE 1-continued

| Type of filler | Percent-age used | Results Appearance | Feel |
|---|---|---|---|
| Polytrap 6603 Poly (methyl methacrylate), aggregates 200 µm to 1200 µm in size. Density: 0.06 | 4% | Opalescent and granular gel. | silky, powdery. The granules cannot be felt. Greasy on application. Does not penetrate. Waxy feel. |
| Zinc oxide U.S.P. (Whittaker Clark) | 4% | White cream, shiny | Greasy, granules are visible but cannot be felt. |

EXAMPLE 1

Anhydrous dermopharmaceutical gel for the treatment of acne:

The following constituents were formulated into a gel:

| (a) Clindamycin phosphate | 1.2% |
|---|---|
| (b) Perhydrosqualene qs | 100% |
| (c) Silicone fluid (245 marketed by Wacker Silicones) | 20% |
| (d) Aerosil R 972 | 8% |
| (e) EI 23 particles | 1% |

The gel obtained was creamy, smooth, shiny and very soft, without a greasy or sticky feel. It could be used on any type of skin tending to be affected by acne.

EXAMPLE 2

Anhydrous dermopharmaceutical gel for the treatment of acne, to be delivered specifically to the follicles:

The following constituents were formulated into a gel:

(a) Orgasol microspheres containing 4.3% of 6-[3-(1-adamantyl)-4-methoxyphenyl]-2-naphthoic acid 2.5%

| (b) Perhydrosqualene qs | 100% |
|---|---|
| (c) Silicone fluid 245 | 20% |
| (d) Aerosil R 972 | 8% |
| (e) EI 23 particles | 1% |

The physical properties of the resulting gel were the same as those of Example 1.

EXAMPLE 3

W/O emulsion for the treatment of dry skins or of xeroses:

Phase A (fatty):

(a) Abil EM 90 marketed by Goldschmidt (cetyldimethicone copolyol) 2.5%

(b) DC 344 Fluid marketed by Dow Corning (cyclomethicone) 15%

(c) DC 593 Fluid marketed by Dow Corning (cyclomethicone) 3.5%

(d) Witconol APM marketed by Witco (polypropylene glycol myristyl ether containing 3 mol of propylene glycol) 6%

Phase B (aqueous):

| | | |
|---|---|---|
| (a') Glycerol | 3% |
| (b') Lactic acid | 5% |
| (c') NH₃ (32% solution) qs | pH 4 |
| (d') NaCl | 0.6% |
| (e') Preservative | 0.15% |
| (f') Water qs | 100% |

Phase C:

| | |
|---|---|
| EI 23 Particles | 1% |

Procedure:

The compounds of the fatty phase were intimately admixed. The emulsion was formed in the cold state using a whirlwind spiral agitator, adding the aqueous phase to the fatty phase with a pipette. The phase C was then added and the components were mixed using the same spiral agitator for 5/10 minutes.

EXAMPLE 4

Anhydrous creamy makeup foundation:

The following constituents were formulated into a cream:

| | |
|---|---|
| (a) Miglyol gel* | 40% |
| (b) Pentadimethylsiloxane | 29% |
| (c) Caprylic/capric acid triglycerides | 14.4% |
| (d) Iron oxide | 1.05% |
| (e) Titanium dioxide | 4.35% |
| (f) EI 23 particles | 0.5% |
| (g) Aerosil R972 | 0.7% |
| (h) Talc (magnesium silicate) | 6% |
| (i) Starch | 4% |
| (j) Preservative qs | |

*Hectorite modified with stearyldimethylbenzylammonium chloride in glyceryl dicaprylate/dicaprate and propylene carbonate.

A very soft, creamy, anhydrous makeup foundation with a nongreasy and nonsticky feel was obtained, despite the high concentration of fats.

EXAMPLE 5

Aqueous deodorant cream (oil/water) (CTFA nomenclature):

Phase A (fatty):

| | |
|---|---|
| (a) Cetearyl alcohol (fat, gelling agent) | 4% |
| (b) Glyceryl stearate (fat, gelling agent) | 2.5% |
| (c) Steareth-25 (emulsifier) | 1.05% |
| (d) Stearyl alcohol (fat, gelling agent) | 1.05% |
| (e) Ceteareth-33 (emulsifier) | 1% |
| (f) Dimethicone | 1% |
| (g) Ceteth-20 (emulsifier) | 0.4% |
| (h) Preservative qs | |

Phase B (aqueous):

| | |
|---|---|
| (a') Water qs | 100% |
| (b') Aluminum chlorohydrate (anitperspirant) | 13% |
| (c,) Preservative qs | |

Phase C (active agent):

| | |
|---|---|
| (a") Perfume qs | |
| (b") Bactericide qs | |

Phase D:

| | |
|---|---|
| EXPANCEL 551 DE 50 | 1% |

Procedure:

The phase B was heated to 70°–80° C. with stirring. The phase A was heated to 70°–80° C. When the two phases were thoroughly homogeneous, phase A was incorporated into phase B with vigorous stirring for 10 min. The mixture was cooled while stirring more gently. At 45° C., the premixed phase C was added. The resulting mixture was stirred vigorously for 5 min. It was cooled while stirring more gently. At about 30° C., the phase D was incorporated slowly. Cooling was continued to room temperature.

A pliant and soft cream was obtained, with a powdered effect on spreading.

EXAMPLE 6

Anhydrous deodorant cream (CTFA nomenclature):

Phase A:

| | |
|---|---|
| (a) Stearalkonium hectorite (gelling agent) | 4.2% |
| (b) Propylene carbonate (suspending agent) | 1.4% |
| (c) Caprylic/capric triglycerides | 29.4% |
| (d) Dimethicone | 5% |
| (e) Isohexadecane (solvent) qs | 100% |

Phase B:

| | |
|---|---|
| (a') Aluminum chlorohydrate (anitperspirant) | 15% |
| (b') EXPANCEL 551 DE 50 | 1% |

Phase C:

| |
|---|
| Perfume qs |

Phase D:

| | |
|---|---|
| Talc | 6% |

Procedure:

The compounds of the phase A were mixed at room temperature. The phase C was then incorporated, also at room temperature. When the mixture was homogeneous, phases B and D were incorporated slowly.

The cream obtained was especially soft, nonfatty and nonsticky, and provided, by means of its dryness, a sensation of greater protection against axillary moisture.

EXAMPLE 7

Aerosol (CTFA nomenclature):

Phase A:

| (a) Cyclomethicone qs | 100% |
|---|---|
| (b) Quaternium-18 bentonite | 3% |
| (c) Triethylcitrate | 7% |
| (d) Dimethiconol | 1.4% |
| (e) Isopropyl palmitate | 6% |

Phase B:

| Aluminum chlorohydrate | 30% |
|---|---|

Phase C:

| EXPANCEL 551 DE 50 | 1.5% |
|---|---|

Procedure:

The ingredients of the phase A were mixed in the cold state. The aluminum chlorohydrate was added slowly, followed by the EXPANCEL. The components were mixed vigorously to obtain a homogeneous suspension. The latter could then be pressurized in the following manner: 13% of liquid, 87% of compressed or liquefied gas.

The applied liquid imparted a soft, powdered sensation to the skin.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A nongreasy, nonsticky cosmetic/dermatological composition comprising at least one fatty substance and an amount of deformable hollow particulates effective to avoid the greasy and/or sticky feel otherwise attributable to said at least one fatty substance, said deformable hollow particulates comprising a copolymer of vinylidene chloride, acrylonitrile and a (meth)acrylic comonomer and having a particle size ranging from 1 μm to 250 μm and further comprising at least one biologically active agent selected from the group consisting of retinoic acid, retinol, 6-[3-(1-adamantyl)-4-methoxyphenyl]-2-naphthoic acid, vitamin D, estradiol, kojic acid, hydroquinone, clindamycin phosphate, erythromycin, metronidazole, econazole, ketoconazole, miconazole, amphotericin B, terbinafine, octopirox, hydrocortisone, betamethasone valerate, clobetasol propionate, ibuprofen, diclofenac, acetylsalicylic acid, paracetamol, glycyrrhetinic acid, lidocaine hydrochloride, thenaldine, trimeprazine, cyproheptadine, acyclovir, salicylic acid, 5-n-octanoylsalicylic acid, glycolic acid, lactic acid, citric acid, alpha-tocopherol, superoxide dismutases, ascorbic acid, progesterone, benzoyl peroxide, and 1,8,10-tripropionyl-9-anthrone.

2. The cosmetic/dermatological composition as defined by claim 1, said deformable hollow particulates having a particle size of less than 100 μm.

3. The cosmetic/dermatological composition as defined by claim 1, said deformable hollow particulates having a particle size ranging from 10 μm to 50 μm.

4. The cosmetic/dermatological composition as defined by claim 1, said deformable hollow particulates having a density ranging from 15 kg/m$^3$ to 200 kg/m$^3$.

5. The cosmetic/dermatological composition as defined by claim 1, said deformable hollow particulates having a density ranging from 40 kg/m$^3$ to 100 kg/m$^3$.

6. The cosmetic/dermatological composition as defined by claim 1, said deformable hollow particulates comprising from 0.01% to 10% of the total weight thereof.

7. The cosmetic/dermatological composition as defined by claim 1, said at least one fatty substance comprising from 0.5% to 99% of the total weight thereof.

8. The cosmetic/dermatological composition as defined by claim 1, said (meth)acrylic comonomer comprising methyl (meth)acrylate.

9. The cosmetic/dermatological composition as defined by claim 1, said at least one fatty substance comprising an oil and/or a wax.

10. The cosmetic/dermatological composition as defined by claim 1, further comprising at least one compound selected from the group consisting of a gelling agent, surfactant, coloring agent, solvent, preservative, perfume, fragrance, hydrating agent, UV-absorber, filler, bactericide, antiperspirant, odor absorber, clay, texturizing agent, lipophilic biologically active agent and a hydrophilic biologically active agent.

11. The cosmetic/dermatological composition as defined by claim 1, said at least one biologically active agent being encapsulated.

12. The cosmetic/dermatological composition as defined by claim 1, wherein said deformable hollow particulates comprise microspheres or microbeads.

13. The cosmetic/dermatological composition as defined by claim 1, which is in the form of a composition selected from the group consisting of a water-in-oil emulsion, a lipophilic gel, and an essentially anhydrous formulation.

14. The cosmetic/dermatological composition as defined by claim 1, which is in the form of a composition selected from the group consisting of a gel, paste, lotion, ointment, salve, and a milk.

15. The cosmetic/dermatological composition as defined by claim 1, which is in the form of a composition selected from the group consisting of a skin cream, a hair care cream, a balm, a blush, a makeup, a dermopharmaceutical preparation, a cleanser, a makeup remover, a deodorant, a sunscreen, a foundation, and an aerosol.

* * * * *